(12) United States Patent
Ohta et al.

(10) Patent No.: US 9,448,238 B2
(45) Date of Patent: Sep. 20, 2016

(54) MONOCLONAL ANTIBODY FOR DETECTING EXOSOMES

(71) Applicant: SHIONOGI & CO., LTD., Osaka-shi, Osaka (JP)

(72) Inventors: Hideki Ohta, Toyonaka (JP); Chihiro Okada, Toyonaka (JP); Tomi Murakami, Toyonaka (JP); Hiroyuki Okamoto, Toyonaka (JP); Hikaru Sonoda, Settsu (JP)

(73) Assignee: COSMO BIO CO., LTD., Tokyo (JP)

( * ) Notice: Subject to any disclaimer, the term of this patent is extended or adjusted under 35 U.S.C. 154(b) by 142 days.

(21) Appl. No.: 14/368,706

(22) PCT Filed: Dec. 26, 2012

(86) PCT No.: PCT/JP2012/083612
§ 371 (c)(1),
(2) Date: Jun. 25, 2014

(87) PCT Pub. No.: WO2013/099925
PCT Pub. Date: Jul. 4, 2013

(65) Prior Publication Data
US 2015/0010913 A1 Jan. 8, 2015

(30) Foreign Application Priority Data

Dec. 26, 2011 (JP) .................. 2011-283928

(51) Int. Cl.
C07K 16/28 (2006.01)
G01N 33/574 (2006.01)
C07K 16/18 (2006.01)
G01N 33/577 (2006.01)
C12Q 1/68 (2006.01)

(52) U.S. Cl.
CPC ............ *G01N 33/574* (2013.01); *C07K 16/18* (2013.01); *C07K 16/2896* (2013.01); *C12Q 1/6804* (2013.01); *C12Q 1/6886* (2013.01); *G01N 33/577* (2013.01); *G01N 2333/70596* (2013.01); *G01N 2500/04* (2013.01)

(58) Field of Classification Search
None
See application file for complete search history.

(56) References Cited

FOREIGN PATENT DOCUMENTS

| WO | WO 99/18198 A1 | 4/1999 |
| WO | WO 2005/092377 A1 | 10/2005 |
| WO | WO 2006/072166 A1 | 7/2006 |
| WO | WO 2009/157623 A1 | 12/2009 |
| WO | WO 2010/065968 A1 | 6/2010 |

OTHER PUBLICATIONS

Aasted, B. and B. Viuff, "Reactivity of monoclonal antibodies to human CD antigens with cells from mink," Veterinary Immunology and Immunopathology (2007), vol. 119, pp. 27-37.

Azorsa et al., "A general approach to the generation of monoclonal antibodies against members of the tetraspanin superfamily using recombinant GST fusion proteins," Journal of Immunological Methods (1999), vol. 229, pp. 35-48.

Charrin et al., "The Major CD9 and CD81 Molecular Partner—Identification and Characterization of the Complexes" The Journal of Biological Chemistry (Apr. 27, 2001), vol. 276, No. 17, pp. 14329-14337.

Higginbottom et al., "Antibody cross-linking of human CD9 and the high affinity immunoglobulin E receptor stimulates secretion from transfected rat basophilic leukaemia cells," Immunology (2000), vol. 99, pp. 546-552.

Lasser et al., "Human saliva, plasma and breast milk exosomes contain RNA: uptake by macrophages," Journal of Translational Medicine (2011), vol. 9, No. 9, pp. 1-8.

Lengweiler et al., "Preparation of Monoclonal Antibodies to Murine Platelet Glycoprotein llb/lla (αIIbβ3) and Other Proteins from Hamster-Mouse Interspecies Hybridomas," Biochemical and Biophysical Research Communications (1999), vol. 262, pp. 167-173.

Logozzi et al., "High Levels of Exosomes Expressing CD63 and Caveolin-1 in Plasma of Melanoma Patients," PLoS ONE (Apr. 2009), vol. 4, No. 4, e5219, pp. 1-10.

Osumi et al., "Development and Assessent of Enzyme Immunoassay for Platelet-derived Microparticles," Thromb. Haemost. (2001), vol. 85, pp. 326-330.

Singethan, K. and J. Schneider-Schaulies, "Tetraspanins—Small transmembrane proteins with big impact on membrane microdomain structures," Communicative & Integrative Biology (Jul./Aug./Sep. 2008), vol. 1, No. 1, pp. 11-13.

Taylor, D. D. and C. Gercel-Taylor, "MicroRNA signatures of tumor-derived exosomes as diagnostic biomarkers of ovarian cancer," Gynecologic Oncology (2008), vol. 110, pp. 13-21.

*Primary Examiner* — Karen Canella
(74) *Attorney, Agent, or Firm* — Birch, Stewart, Kolasch & Birch, LLP

(57) ABSTRACT

A monoclonal antibody for detecting or capturing an exosome, selected from the group consisting of a monoclonal antibody or antibody fragments thereof that recognize amino acid numbers 113 to 195 of the amino acid sequence as shown in SEQ ID NO: 1, a monoclonal antibody or antibody fragments thereof that recognize amino acid numbers 104 to 202 of the amino acid sequence as shown in SEQ ID NO: 2, a monoclonal antibody or antibody fragments thereof that recognize amino acid numbers 36 to 54 of the amino acid sequence as shown in SEQ ID NO: 3, and a monoclonal antibody or antibody fragments thereof that recognize amino acid numbers 113 to 201 of the amino acid sequence as shown in SEQ ID NO: 3, each capable of detecting or capturing an exosome. The monoclonal antibody for detecting an exosome of the present invention is capable of detecting CD9, CD63 or CD81 on the exosome in a living body with an excellent sensitivity and specificity.

4 Claims, 9 Drawing Sheets

A: Small Loop Antigenic Peptide

CD9:   C-R(36)FDSQTKSIFEQETN(50)

CD63:  C-V(38)LSQTIIQGATPGSLLP(54)

B: Large Loop-Fc Fusion Protein

CD9:   H(113) to I(195)

CD63:  G(104) to N(202)

Antibody of the Present Invention: *1: p<0.05, *2: p<0.01
Commercially Available Antibody: *3: p>0.05, *2: p>0.05

Antibody of the Present Invention: *1: p<0.05, *2: p<0.01
Commercially Available Antibody: *3: p>0.05, *4: p>0.05

*1: p<0.01, *2: p<0.01

*1: p<0.01, *2: p<0.01

* 1: p<0.01, *2: p<0.02

* 1: p>0.05, *2: p<0.01

A: Small Loop Antigenic Peptide

CD81: C-R(36)HDPQTTNLLYLELGDKPA(54)

B: Large Loop-Fc Fusion Protein

CD81: F(113) to K(201)

1. Commercially Available Antibody IVA50 (Abnova)
2. Antibody Made in House 12A12
3. Control Antibody 1. Commercially Available Antibody H5C6 (BD)
2. Commercially Available Antibody MEM-259(ExBio)
3. Antibody Made in House 5C1
4. Antibody Made in House 7C10
5. Antibody Made in House 8A12
6. Antibody Made in House 13C8
7. Without Antibody

MONOCLONAL ANTIBODY FOR DETECTING EXOSOMES

TECHNICAL FIELD

The present invention relates to a set of antibodies for detecting an exosome. More particularly, the present invention relates to a monoclonal antibody against a particular antigen (CD9, CD63, CD81) on an exosomal surface or an antibody fragment thereof, a set containing the monoclonal antibodies or antibody fragments thereof, a method for detecting miRNA derived from an exosome using the monoclonal antibody or antibody fragments thereof, a method for measuring a complex formed between the set and a biological sample derived from an individual to be tested, a method for diagnosing cancer or an immune disease using the set and a kit for carrying out the method, and a method for evaluating drug efficacy of an anticancer agent or an anti-immune disease drug using the set and a kit for carrying out the method.

BACKGROUND ART

An exosome is a granular vesicle existing in a body fluid in a living body. It is known that a wide variety of membrane proteins exist on an exosomal surface, as in the case with a general cell surface. On the other hand, it has also become known that microRNA (miRNA) is contained inside an exosome, in addition to various proteins such as cytokines. In addition, it has been also reported that exosomes are secreted from various kinds of cells, for example, cells of the immune system and various cancer cells, and the function as an intermediary in intercellular communication in a living body to be associated with physiological phenomena and association with a disease such as cancer have been remarked.

For example, it has been reported in Non-Patent Publication 1 that an exosome in the circulating blood of a patient with ovarian cancer are isolated using an antibody against EpCAM, which is a tumor marker, and association between an expression level of miRNA derived from an exosome and patients with ovarian cancer is found. Accordingly, if a quantitative change in an exosome associated with a disease such as cancer can be easily grasped, its application to a diagnostic drug can be expected.

In addition, CD9, CD63 and CD81 are four-transmembrane membrane proteins belonging to tetraspanin family, and expressed on many exosomes. For example, it has been reported in Non-Patent Document 2 that an exosome in plasma of melanoma patients are detected and quantified with an antibody against CD63 and an antibody against a tumor-associated marker Caveolin-1, and that the exosomes increased as compared to those of normal individuals. In Patent Document 1, signals ascribed to exosomes in cancer patients are quantified and analyzed by subjecting centrifuged plasma samples to a reaction in combination with anti-CD63 antibodies, antibodies against various membrane proteins, and the like.

PRIOR ART REFERENCES

Patent Publications

Patent Publication 1: WO 2010/065968

Non-Patent Publications

Non-Patent Publication 1: D. D. Taylor, et al., *Gynecol. Oncol.*, 2008, 110, 13-21

Non-Patent Publication 2: M. Logozzi, et al., *PLoS ONE*, 2009, 4, 1-10

SUMMARY OF THE INVENTION

Problems to be Solved by the Invention

As anti-CD9 antibodies, anti-CD63 antibodies and anti-CD81 antibodies, various antibodies are sold. These commercially available antibodies are one of the antibodies which are obtained as a result of directly immunizing cells which express CD9, CD63 or CD81, not antibodies obtained by carrying out immunization with designed particular antigens. For this reason, these antibodies are still insufficient in terms of sensitivity and specificity, and the development of further techniques is needed in order to detect an exosome not only quickly and simply, but also accurately and precisely.

An object of the present invention is to provide a monoclonal antibody or an antibody fragment thereof capable of detecting or capturing an exosome in a living body with excellent sensitivity and specificity, a set containing the monoclonal antibodies or antibody fragments thereof, a method for measuring a complex formed between the set and a biological sample derived from an individual to be tested, a method for diagnosing cancer or an immune disease using the set, and a method for evaluating drug efficacy of an anticancer agent or an anti-immune disease drug using the set.

Means to Solve the Problems

As a result of intensive studies in order to solve the above-mentioned problems, the present inventors have found that an exosome in a living body can be detected and captured with excellent sensitivity and specificity by preparing and using monoclonal antibodies against particular sequences of CD9, CD63 and CD81 on exosomes. The present invention has been perfected thereby.

Concretely, the present invention relates to:

<1> A monoclonal antibody for detecting or capturing an exosome selected from the group consisting of a monoclonal antibody or antibody fragments thereof that recognize amino acid numbers 113 to 195 of the amino acid sequence as shown in SEQ ID NO: 1, a monoclonal antibody or antibody fragments thereof that recognize amino acid numbers 104 to 202 of the amino acid sequence as shown in SEQ ID NO: 2, a monoclonal antibody or antibody fragments thereof that recognize amino acid numbers 36 to 54 of the amino acid sequence as shown in SEQ ID NO: 3, and a monoclonal antibody or antibody fragments thereof that recognize amino acid numbers 113 to 201 of the amino acid sequence as shown in SEQ ID NO: 3, each capable of detecting or capturing an exosome.

More particularly, the present invention relates to the following <2> to <13>:

<2> A monoclonal antibody for detecting or capturing an exosome selected from the group consisting of:

a monoclonal antibody (CD9-12A12 antibody) produced by a hybridoma deposited under Accession Number FERM BP-11519 or fragments thereof, that recognize amino acid numbers 113 to 195 of the amino acid sequence as shown in SEQ ID NO: 1;

a monoclonal antibody (CD63-8A12 antibody) produced by a hybridoma deposited under Accession Number FERM BP-11520 or fragments thereof, that recognize amino acid numbers 104 to 202 of the amino acid sequence as shown in SEQ ID NO: 2;

a monoclonal antibody (CD63-13C8 antibody) produced by a hybridoma deposited under Accession Number FERM BP-11521 or fragments thereof, that recognize amino acid numbers 104 to 202 of the amino acid sequence as shown in SEQ ID NO: 2;

a monoclonal antibody (CD81-4G6 antibody) produced by a hybridoma deposited under Accession Number NITE BP-1480 or fragments thereof, that recognize amino acid numbers 113 to 201 of the amino acid sequence as shown in SEQ ID NO: 3;

a monoclonal antibody (CD81-6D12 antibody) produced by a hybridoma deposited under Accession Number NITE BP-1481 or fragments thereof, that recognize amino acid numbers 113 to 201 of the amino acid sequence as shown in SEQ ID NO: 3; and a monoclonal antibody (CD81-12C4 antibody) produced by a hybridoma deposited under Accession Number NITE BP-1482 or fragments thereof, that recognize amino acid numbers 36 to 54 of the amino acid sequence as shown in SEQ ID NO: 3.

<3> A set of monoclonal antibodies or antibody fragments thereof, containing a combination of the same or two monoclonal antibodies or antibody fragments selected from the group consisting of a CD9-12A12 antibody or antibody fragments thereof, a CD63-8A12 antibody or antibody fragments thereof, and a CD63-13C8 antibody or antibody fragments thereof.

<4> The set according to the above <3>, which is selected from the group consisting of:

a set wherein an immobilized antibody is a CD9-12A12 antibody or an antibody fragment thereof, and a labeled antibody is a CD9-12A12 antibody or an antibody fragment thereof;

a set wherein an immobilized antibody is a CD9-12A12 antibody or an antibody fragment thereof, and a labeled antibody is a CD63-13C8 antibody or an antibody fragment thereof;

a set wherein an immobilized antibody is a CD63-8A12 antibody or an antibody fragment thereof, and a labeled antibody is a CD9-12A12 antibody or an antibody fragment thereof; and a set wherein an immobilized antibody is a CD63-8A12 antibody or an antibody fragment thereof, and a labeled antibody is a CD63-13C8 antibody or an antibody fragment thereof.

<5> The set according to the above <3> or <4>, for use in detection of an exosome.

<6> A set of a monoclonal antibody for detecting a disease-specific exosome, containing a combination of an antibody or antibody fragments thereof, selected from the group consisting of a CD9-12A12 antibody or antibody fragments thereof, a CD63-8A12 antibody or antibody fragments thereof, and a CD63-13C8 antibody or antibody fragments thereof, and an antibody or antibody fragments thereof against a disease-specific membrane protein.

<7> A diagnostic kit for cancer or an immune disease, containing monoclonal antibodies or antibody fragments thereof of a set as defined in any one of the above <3> to <5>.

<8> A diagnostic kit for cancer or an immune disease, containing monoclonal antibodies or antibody fragments thereof of a set as defined in the above <6>.

<9> A diagnostic kit for cancer or an immune disease, containing a set as defined in the above <6>.

<10> A method for detecting miRNA of an exosome, including contacting a biological sample derived from an individual to be tested with a monoclonal antibody as defined in the above <1> or <2>, and capturing the exosome.

<11> A method for measuring a signal intensity ascribed to an exosome complex, including contacting a biological sample derived from an individual to be tested with a monoclonal antibody of a set as defined in any one of the above <3> to <5> to form the exosome complex.

<12> A method for judging cancer or an immune disease, which is a method for judging whether or not an individual to be tested has an onset of cancer or an immune disease, including:

step (I): contacting a biological sample derived from an individual to be tested with a monoclonal antibody of a set as defined in any one of the above <3> to <5> to form an exosome complex, and measuring a signal intensity ascribed to the complex; and step (II): comparing the signal intensity measured in the above step (I) and a signal intensity of a control individual, and judging that the above individual to be tested has an onset of cancer or an immune disease in a case where the signal intensity in the above individual to be tested is recognized to be more intense than the signal intensity of the control individual.

<13> A method for evaluating drug efficacy of an anticancer agent or an anti-immune disease drug, including:

step (A): contacting biological samples derived from an individual to be tested before and after administration of the anticancer agent or the anti-immune disease drug with a monoclonal antibody of a set as defined in any one of the above <3> to <5> to form exosome complexes, and measuring signal intensities ascribed to the complexes; and step (B): judging that it is highly possible to show the drug efficacy of the anticancer agent or the anti-immune disease drug, in a case where the signal intensity of the complex in the biological sample derived from the individual to be tested after administration of the anticancer agent or the anti-immune disease drug are recognized to be weaker than the signal intensity in the biological samples derived from the individual before administration of the anticancer agent or the anti-immune disease drug.

Effects of the Invention

The monoclonal antibody for detecting an exosome of the present invention can detect and capture CD9, CD63 or CD81 on an exosome in a living body with excellent sensitivity and specificity. Therefore, some excellent effects are exhibited that a slight change in exosomes in a blood specimen (including a change in the amount of a membrane protein on an exosome CD9, CD63 or CD81, in addition to quantitative change in exosomes) can be captured, thereby making it possible to detect a change in exosomes derived from a disease such as cancer, so that the antibody can be applied to the diagnosis of a disease which causes the change.

MODES FOR CARRYING OUT THE INVENTION

The monoclonal antibody for detecting an exosome of the present invention has a feature that the monoclonal antibody is capable of detecting or capturing CD9, CD63 or CD81 on an exosome in a living body with excellent sensitivity and specificity. Accordingly, the monoclonal antibody of the present invention may be also described as a monoclonal antibody for detecting or capturing an exosome.

CD9, CD63 and CD81 on exosomes are a polypeptide consisting of an amino acid sequence as shown in SEQ ID NO: 1, a polypeptide consisting of an amino acid sequence as shown in SEQ ID NO: 2, and a polypeptide consisting of an amino acid sequence as shown in SEQ ID NO: 3, respectively. In addition, all of CD9, CD63 and CD81 are membrane proteins belonging to the tetraspanin family which have a four-transmembrane structure shown in FIG. 2A. These membrane proteins extracellularly present two kinds of loop structures, a small loop (referred to as EC1) and a large loop (referred to as EC2). The monoclonal antibody of the present invention has the feature of showing a specific recognition for these loops.

A method for preparing a monoclonal antibody for detecting or capturing exosomes of the present invention, a set containing the antibody, an evaluation method using the antibody or set, and capture of exosomes using the antibody will be hereinbelow described in detail.

<Method for Preparing Monoclonal Antibody>
(Preparation of Antigen)

Since the monoclonal antibody of the present invention is prepared by designing an antigen as described below, the monoclonal antibody is excellent in sensitivity and specificity to the antigen.

Figure 1:
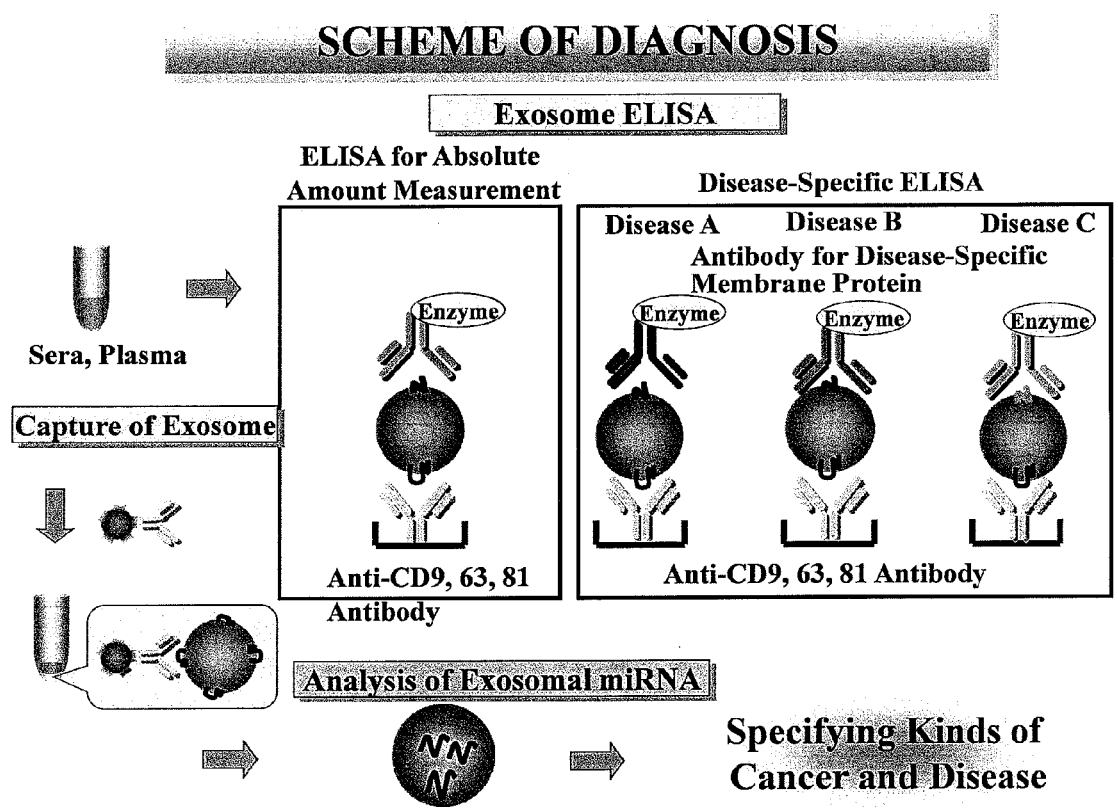
FIG. 1 is a scheme showing the concept of a diagnostic method utilizing an exosome.
Figure 2:
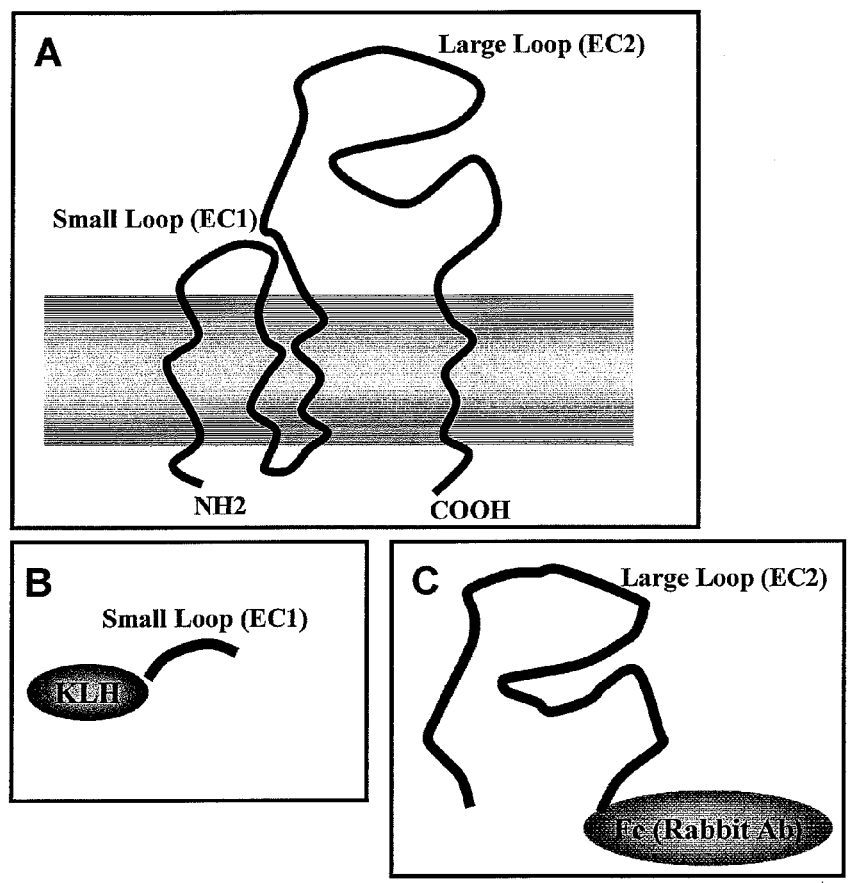
FIG. 2 is a diagram showing the structure of tetraspanin family (CD9, CD63 and CD81) (FIG. A), and diagrams showing a small loop peptide conjugate (FIG. B) and a large loop-Fc fusion protein (FIG. C) used in the preparation of an antibody.

A small loop peptide of CD9, CD63 or CD81 of an exosome, in other words, a peptide in which a cysteine residue is added to an amino terminal of Arg36-Asn50 of a CD9 polypeptide, Val38-Pro54 of a CD63 polypeptide or Arg36-Ala54 of a CD81 polypeptide is synthesized in accordance with a known method. For each of the obtained peptides, a hapten antigen is prepared via an SH group of the peptide, using a maleimidated KLH [Keyhole Limpet Hemocyanin, Imject (registered trademark) Maleimide Activated mcKLH, manufactured by Pierce Biotechnology, Inc.]. A schematic view of the above-mentioned immunogens is shown in FIG. 2B, and the peptide sequences thereof are shown in FIG. 3A and FIG. 12A.

In addition, a fusion protein of Fc region of rabbit IgG and a large loop peptide of CD9, CD63 or CD81 (Fc fusion protein) can also be used as an antigen. Concretely, the fusion protein can be prepared by introducing a plasmid vector having insertion of a polynucleotide sequence corresponding to a polypeptide of Fc added to a carboxyl terminal of His113-Ile195 of a CD9 polypeptide, Gly104-Asn202 of a CD63 polypeptide or Phe113-Lys201 of a CD81 polypeptide into, for example, Freestyle 293-F Cells (manufactured by Invitrogen Corporation) to thereby transiently express the polypeptide, and thereafter purifying the polypeptide using a protein A column (MAPS II Kit, Bio-Rad Laboratories, Inc.). A schematic view of the above-mentioned immunogens is shown in FIG. 2C, and the peptide sequences thereof are shown in FIG. 3B and FIG. 12B.

(Preparation of Monoclonal Antibody)

The monoclonal antibody for detecting an exosome of the present invention (hereinafter also simply referred to as the monoclonal antibody of the present invention) is not particularly limited, and can be prepared in accordance with a known method, for example, the method described in K. Watanabe et al., Vasohibin as an endothelium-derived negative feedback regulator of angiogenesis, *J. Clin. Invest.* 114 (2004), 898-907.

Concretely, first, a mammal is immunized using an antigen obtained as described above. The mammal is not particularly limited, and, in general, a mouse, rat, bovine, rabbit, goat, sheep, guinea pig or the like can be used. Among them, a mouse and rat are preferred, and a mouse is more preferred. The mouse is exemplified by A/J type, BALB/C type, DBA/2 type, C57BL/6 type mice. In addition, the age of the mammal differs depending on the animal species to be used and not particularly limited, and, usually about 4 to about 12 weeks old, and preferably about 5 to about 10 weeks old, in a case of a mouse or rat. Here, these mammals can be selected taking into consideration compatibility with plasma cells to be subjected to cell fusion, for the production of the monoclonal antibody of the present invention.

The antigen is mixed with an adjuvant in order to enhance immune response to be used as an immunogen. The adjuvant is not particularly limited, and a known adjuvant can be used. In addition, mixing of the adjuvant and the antigen can be carried out in accordance with a method known in the art in regard to the adjuvant to be used.

Immunization of a mammal is carried out in accordance with a method known in the art. For example, the immunization is carried out by administering an immunogen to a mammal by administration of subcutaneous, intradermal, intravenous and/or intraperitoneal injection. In addition, the administration of the immunogen may be repeatedly carried out several times after the first immunization, and dosing intervals thereof can be appropriately adjusted. Here, since immune response differs depending on the kinds and strains of the mammals to be immunized, the immunization schedule and the dose of the immunogen may be appropriately set in accordance with the animals to be used.

Thus, a desired antibody-producing cell can be prepared in the body of an immunized mammal. As the antibody-producing cell, a spleen cell excised after 3 to 5 days from a final administration of the immunogen is preferred. Here, in order to allow hypertrophy of the spleen of the immunized mammal, booster (additional injection of an immunogen) may be carried out. The amount of the immunogen to be administered by booster is preferably about 4 to about 5 times the amount of the immunogen to be first administered, but can be appropriately increased or decreased with this amount as a measure.

Next, the obtained antibody-producing cell is subjected to cell fusion with a cell derived from myeloma (myeloma cell), to prepare a hybridoma.

Since the proliferative ability of a hybridoma depends on the kind of the myeloma cell usable in the cell fusion, the myeloma cell is preferably a cell which is excellent in proliferative ability. In addition, it is preferable that the myeloma cell is compatible with the mammal from which the antibody-producing cell to be fused is originated. As examples thereof, myeloma cells are exemplified by mouse myeloma P3U1 and X63-Ag8.653 and the like.

As a method for cell fusion, a method known in the art can be used, which is exemplified by, for example, a method using polyethylene glycol (PEG), a method using Sendai virus, a method using an electrofusion device, and the like.

The obtained hybridoma can be separated by culturing the hybridoma in a selective medium in accordance with a known method. Here, in order to confirm whether or not a selected hybridoma produces the desired antibody, the culture supernatant is collected, and antibody titer assay can be carried out on the basis of a known method, for example, ELISA method described later.

Thus, a hybridoma which produces a desired monoclonal antibody is obtained. The hybridoma can be subcultured in an ordinary medium, or can also be semi-permanently stored in a liquid nitrogen.

The desired monoclonal antibody can be mass-produced by in vivo and in vitro culture methods. An in vitro culture method can be carried out by culturing a hybridoma in an appropriate serum medium or a serum-free medium, to produce a desired monoclonal antibody in the medium. According to this culture method, a desired antibody having relatively high purity can be obtained as a culture supernatant. In addition, an in vivo culture method can be carried out by injecting a hybridoma intraperitoneally to a mammal compatible with the hybridoma, for example, a mouse, and a desired antibody can be collected in a large amount as mouse ascites.

The obtained culture supernatant and ascites of a mouse or the like can be used directly as a crude antibody solution. In addition, these culture supernatant and ascites can be purified in accordance with a conventional method, for example, by a proper combination of DEAE anion exchange chromatography, affinity chromatography, ammonium sulfate fractionation, PEG fractionation, ethanol fractionation and the like, to give a purified antibody.

The monoclonal antibody of the present invention thus obtained is shown in Table 1. In the present specification, each monoclonal antibody can be identified by an antigenic protein and a clone number, and can be identified as, for example, a CD9-12A12 antibody.

TABLE 1

| Antigen | Clone No. | Subclass | Epitope |
|---------|-----------|----------|---------|
| CD9     | 12A12     | IgG2b    | H113-I195 |
| CD63    | 8A12      | IgG2a    | G104-N202 |
|         | 13C8      | IgG1     | G104-N202 |
| CD81    | 4G6       | IgG1     | F113-K201 |
|         | 6D12      | IgG2a    | F113-K201 |
|         | 12C4      | IgG2a    | R36-A54 |

Here, in the present invention, as the hybridoma which produces the above-mentioned monoclonal antibody, cells deposited at International Patent Organism Depositary, National Institute of Technology and Evaluation, Incorporated Administrative Agency (Tsukuba Central 6, 1-1-1 Higashi, Tsukuba, Ibaraki-ken, Japan or 2-5-8 Kazusakamatari, Kisarazu-shi, Chiba-ken, Japan) under the accession numbers given hereinbelow can also be used:

FERM BP-11519 (the monoclonal antibody produced is a CD9-12A12 antibody, identification: CD9:12A12, date of acceptance: Nov. 8, 2011)

FERM BP-11520 (the monoclonal antibody produced is a CD63-8A12 antibody, identification: CD63:8A12, date of acceptance: Nov. 8, 2011)

FERM BP-11521 (the monoclonal antibody produced is a CD63-13C8 antibody, identification: CD63:13C8, date of acceptance: Nov. 8, 2011).

NITE BP-1480 (the monoclonal antibody produced is a CD81-4G6 antibody, identification: CD81-4G6, date of acceptance: Dec. 12, 2012)

NITE BP-1481 (the monoclonal antibody produced is a CD81-6D12 antibody, identification: CD81-6D12, date of acceptance: Dec. 12, 2012)

NITE BP-1482 (the monoclonal antibody produced is a CD81-12C4 antibody, identification: CD81-12C4, date of acceptance: Dec. 12, 2012)

All restrictions imposed on the availability of the public of the deposited materials FERM BP-11519, FERM BP-11520, FERM BP-11521, NITE BP-1480, NITE BP-1481, and NITE BP-1482 will be irrevocably removed upon the granting a patent for the same.

In the present invention, a "monoclonal antibody fragment" means a part of a monoclonal antibody of the present invention mentioned above, the fragment having a specific binding property to CD9, CD63 or CD81 in the same manner as in the monoclonal antibody. The fragment having a specific binding property to CD9, CD63 or CD81 concretely includes peptides including Fab, F(ab')$_2$, Fab', a single-chain antibody (scFv), a disulfide-stabilized antibody (dsFv), a dimerized V region fragment (Diabody), CDR, and the like (*Expert Opinion on Therapeutic Patents* 1996, 6(5), 441-456).

Since the monoclonal antibody or an antibody fragment thereof of the present invention exhibits a specific recognition against CD9, CD63 or CD81 on the exosomal surface, the monoclonal antibody or an antibody fragment thereof is preferably used for the evaluation method described later for a substance which expresses CD9, CD63 or CD81 as a subject.

<Set of Monoclonal Antibodies>

In addition, the present invention provides a set of monoclonal antibodies containing at least one kind of a monoclonal antibody or an antibody fragment thereof of the present invention. By using the above set, exosomal captures in a sample can be carried out with a high sensitivity, whereby, for example, a quantitative precision according to a sandwich ELISA method is improved.

The set includes the following two embodiments, depending upon the kinds of antibodies to be combined with the monoclonal antibody of the present invention.

Embodiment 1: a set containing two or more kinds of monoclonal antibodies or antibody fragments thereof of the present invention Embodiment 2: a set containing a monoclonal antibody or an antibody fragment thereof of the present invention and an antibody or an antibody fragment thereof against a disease-specific membrane protein The set of Embodiment 1 is not particularly limited, so long as the set contains two or more kinds of monoclonal antibodies or antibody fragments thereof of the present invention, and the set also includes embodiments which contains a plurality of homologous antibodies or antibody fragments thereof. Concrete examples include a set of an antibody selected from the group consisting of a CD9-12A12 antibody or an antibody fragment thereof, a CD63-8A12 antibody or an antibody fragment thereof, and a CD63-13C8 antibody or an antibody fragment thereof, combined with an antibody selected from the group consisting of a CD9-12A12 antibody or an antibody fragment thereof, a CD63-8A12 antibody or an antibody fragment thereof, and a CD63-13C8 antibody or an antibody fragment thereof. In this case, one can be used as an immobilized antibody, and the other can be used as a labeled antibody.

The preparation of an immobilized antibody and a labeled antibody, in other words, the immobilization and labelling of the monoclonal antibody or an antibody fragment thereof listed in Table 1 can be carried out in accordance with a known method without particularly limitations.

The combination of the immobilized antibody and the labeled antibody can be evaluated in accordance with a known ELISA method, for example, by examining a specific binding property or quantification of exosomes.

The specific binding property can be evaluated by a signal intensity obtained when measuring exosomes in a sample to which a known amount of exosomes is added according to a sandwich ELISA method described in Example 4 given later. A combination that gives a sufficient signal intensity is judged as an excellent combination. Furthermore, a spike and recovery test of exosomes on a blood specimen is conducted, which can also be used for judgment for selection of the combination of being excellent or poor in additional recovery. For example, a combination is judged as an excellent combination when additional recovery is from 85 to 115% or so.

Regarding quantification, in a method similar to a sandwich ELISA method described in Example 4 given later, a combination that is acknowledged to show an increase in a signal intensity observed in an exosomal concentration-dependent manner within a concentration range of at least up to 100 ng/mL, and preferably from 50 to 25,000 ng/mL and a combination that gives a standard curve having excellent linearity can be judged as an excellent combination.

As described above, the combinations that are judged as excellent combinations are shown in Table 2 given hereinbelow.

TABLE 2

| Immobilized Antibody | Labelled Antibody |
|---|---|
| CD9-12A12 | CD9-12A12 |
| CD63-8A12 | CD63-13C8 |

A concrete method for using a set of Embodiment 1 will be explained in the measurement method described later.

A set of Embodiment 2 contains a monoclonal antibody or an antibody fragment thereof of the present invention and an antibody or an antibody fragment thereof against a disease-specific membrane protein. Concrete examples include a set of an antibody selected from the group consisting of a CD9-12A12 antibody or an antibody fragment thereof, a CD63-8A12 antibody or an antibody fragment thereof, and a CD63-13C8 antibody or an antibody fragment thereof, combined with an antibody or an antibody fragment thereof against a disease-specific membrane protein. In this case, either one of them can be used for immobilizing exosomes (also referred to as for immobilizing exosomes), and the other one can be used for labelling exosomes. However, from the viewpoint of immobilizing exosomes and discriminating whether or not the exosomes are specific for a disease, it is preferable that the monoclonal antibody of the present invention is used for immobilizing exosomes, and that an antibody against a disease-specific membrane protein is used for labelling exosomes. Here, an antibody against a disease-specific membrane protein as used herein means an antibody against a disease-specific membrane protein existing on the exosomal surface. The antibody includes, for example, Ep-CAM, EGFR, CD276, CD55, CD71, EphA2, PSMA, Integrin, HER2 and HER3.

A concrete method for using a set of Embodiment 2 will be explained in the measurement method described later.

<Evaluation Method Utilizing Monoclonal Antibody or Set of the Present Invention>

(Secondary Evaluation of Antibody)

The binding property of a test antibody to CD9 or CD63 can be evaluated by allowing any given test antibody to act on VLPs (Virus-Like Particles) forcibly expressing CD9 or CD63.

Concretely, VLPs forcibly expressing CD9 or CD63 and a type I membrane protein (for example, TEM7) are added to a plate immobilized with an anti-mouse IgG antibody, and further each of an anti-CD test antibody and a labeled antibody against a type I membrane protein (for example, HRP-labeled anti-TEM7 antibody Fab') are added thereto, to carry out a reaction. After the reaction, the plate is washed, and the remaining VLPs are quantified by detecting the label of the antibody (in the above-mentioned example, HRP activity labeled in the antibody will be detected). It can be evaluated that the more the remaining VLPs are, the more excellent the binding property of the test antibody.

(Method for Capturing Exosome)

When subjected to exosomal captures, a monoclonal antibody of the present invention is preferably used. For example, a monoclonal antibody of the present invention is biotinylated, and allowed to react with an exosome, and the reacted exosome can be isolated using streptavidin-immobilized magnetic beads.

More particularly, first, a monoclonal antibody or an antibody fragment thereof of the present invention is biotinylated in accordance with a known method. Next, an exosome and a biotinylated antibody are mixed, and allowed to react at 4° C. overnight. Thereafter, streptavidin-immobilized magnetic beads are added thereto, and allowed to react at 4° C. for additional 2 hours, and thereafter separation is carried out using a magnet, thereby exosomes binding to the biotinylated antibody can be recovered.

(Method for Detecting miRNA Derived from Exosome)

Exosomes are secreted from a wide variety of cells, for example, cells of the immune system or various cancer cells. Thus, if miRNA derived from exosomes can be detected, physiological phenomena and various diseases can be judged by analyzing the results.

Concretely, a biological sample derived from an individual to be tested and a monoclonal antibody or an antibody fragment thereof of the present invention are contacted, and an exosome is isolated in accordance with the above-mentioned method for capturing and separating an exosome. From the collected exosome, miRNA is detected in accordance with a known method.

The detected miRNA can be analyzed in accordance with a known method, thereby making it possible to analyze physiological phenomena and to judge that it is suffering from a particular disease.

Here, in the present specification, a biological sample is not particularly limited, so long as the biological sample is selected from the group consisting of blood, serum and plasma.

(Immunoassay Method)

Immunoassay is carried out using a set of the monoclonal antibodies of the present invention. The immunoassay method includes enzyme immunoassay (EIA), enzyme-linked immunosorbent assay (ELISA), fluorescent immunoassay (FIA), radioactive immunoassay (RIA), luminescent immunoassay, immunoblot method, Western blot method and the like. The ELISA method is preferred, because the method can detect an antibody conveniently and highly sensitively.

The ELISA method includes a general competitive method, sandwich method and the like. The sandwich method is preferred, because the monoclonal antibody or an antibody fragment thereof of the present invention can be used for the immobilized antibody or for both the immobilized antibody and the labeled antibody in the sandwich method.

Next, one embodiment of a sandwich ELISA method will be shown. First, the monoclonal antibody or an antibody fragment thereof of the present invention is immobilized, and thereafter contacted with a test sample containing an exosome, to form a complex. Thereafter, of the sets of the present invention, the other monoclonal antibody or an antibody fragment thereof of the present invention in the case of Embodiment 1, or an antibody or an antibody fragment thereof against a disease-specific membrane protein in the case of Embodiment 2, is respectively added to a modified, labeled antibody to form a further complex, and the label is detected, and thereby the amount of signals ascribed to exosomes contained in the sample in the case of Embodiment 1 or the amount of a disease-specific exosome contained in the sample in the case of Embodiment 2 can be respectively measured. Therefore, the present invention also provides a method for measuring an existing level of a complex including contacting a biological sample derived from an individual to be tested with a monoclonal antibody contained in the set of the monoclonal antibody of the present invention to form the complex.

Here, when immobilizing the monoclonal antibody or an antibody fragment thereof of the present invention, the immobilization may be carried out by direct immobilization or via a known adaptor, for example, streptavidin.

(Prediction of Onset of Cancer or Immune Disease)

In addition, the present invention provides a method for diagnosing cancer or an immune disease (method for predicting an onset). The set of Embodiment 1 of the present invention is capable of detecting exosomes distributed in a living body with excellent sensitivity and specificity. The set of Embodiment 2 is capable of detecting a disease-specific exosome with excellent sensitivity. Since exosomes are secreted from various cells, for example, cells of the immune system or various cancer cells, it is thought that the amount of exosomes in a living body becomes large in the case of having an onset of cancer or an immune disease. In addition, in a cancer cell or the like, it is possible that changes occur on the cell surface as compared to a normal cell, and that the expression level of a membrane protein such as CD9 or CD63 is increased. Therefore, cancer or an immune disease (prediction of an onset) can be diagnosed by using the amount of the signals ascribed to exosomes as an index. Furthermore, in the case of Embodiment 2, it is also possible to specify the cancer or immune disease, and the method can also be used as a diagnostic method (method for measuring or method for judging an onset-associated factor).

The cancer or an immune disease of which onset can be diagnosed is exemplified by cancer diseases such as colorectal cancer, breast cancer, cancer of the uterine body, cervical cancer, ovarian cancer, pancreatic cancer, gastric cancer, esophageal cancer, liver cancer, lung cancer, renal cancer, and skin cancer; and inflammatory diseases such as rheumatoid arthritis, osteoarthritis, nephropathy (diabetic nephropathy and glomerular nephritis), pancreatitis, hepatitis and allergy. In addition, if the diagnosis is applied as an index of immunoreactivity of a cytotoxic T-cell (CTL), the diagnosis can also be applied for judgment of an effect of a cancer vaccine on a cancer disease.

Concretely, the above-mentioned prediction method includes, a method for judging cancer or an immune disease, including:

step (I): contacting a biological sample derived from an individual to be tested with a monoclonal antibody of the set of the present invention to form an exosome complex, and measuring a signal intensity ascribed to the complex; and step (II): comparing a signal intensity measured in the above step (I) and a signal intensity of a control individual, and judging that the individual to be tested has an onset of cancer or an immune disease in a case where the signal intensity in the above individual to be tested is recognized to be more intense than the signal intensity of the control individual.

For the measurement of the signal intensity ascribed to the complex in the step (I) in the above-mentioned prediction method, a method well known to one of ordinary skill in the art can be used, so long as the method is a method using a monoclonal antibody of the present invention, and a sandwich ELISA method is preferred.

In the step (II), regarding the signal intensity obtained the above, a comparison is made by carrying out a statistical analysis on the basis of the signal in the control individual. The analysis method is not particularly limited, and a known method can be used. In addition, in the subsequent judgment, for example, it is judged that it is highly possible that the individual to be tested has an onset of cancer or an immune disease in a case where the signal of the biological sample derived from an individual to be tested is more than the signal in the control individual. Here, in the present invention, the control individual refers to an average of individuals of the same age-group and the same gender who do not have an onset of cancer or an immune disease. The signal intensity in the control individual can be measured at the same time with the signal intensity in the individual to be tested, or a statistic separately obtained from previously measured values can be used.

(Kit for Predicting Onset of Cancer or Immune Disease)

In another embodiment of the present invention, a kit for diagnosing cancer or an immune disease is provided.

The kit of the present invention includes a kit containing the set of monoclonal antibodies of the present invention, and the above-mentioned kit can be used so long as the kit is used for a detection method using the set of the monoclonal antibodies of the present invention when detecting exosomes in a sample. Since the set of monoclonal antibodies of the present invention can detect exosomes in a living body with excellent sensitivity and specificity, use of the kit can contribute much to the diagnosis of cancer or an immune disease.

(Evaluation of Drug Efficacy of Anticancer Agent)

In addition, in another embodiment of the present invention, a method for evaluating drug efficacy of an anticancer agent or an anti-immune disease drug is provided.

Since exosomes are secreted from a wide variety of cells, for example, cells of the immune system or various cancer cells, it is thought that the drug efficacy in a patient can be evaluated by measuring change in exosomes in blood (including a change in the amount of a membrane protein, in addition to increase or decrease in the existing amount) of before and after the administration of an anticancer agent or anti-immune disease drug. In addition, for example, it is thought that, if an antibody or an antibody fragment thereof against a membrane protein specific for a cancer cell is combined with the monoclonal antibody or an antibody fragment of the present invention, improvement in specificity of cancer diagnosis and specification of the kind of cancer can be expected, thereby making it possible to develop a diagnostic drug which is more specific for a cancer disease.

Concretely, the above-mentioned method for evaluating drug efficacy of an anticancer agent or an anti-immune disease drug includes:

step (A): contacting biological samples derived from an individual to be tested before and after administration of the anticancer agent or the anti-immune disease drug with a monoclonal antibody contained in the set of monoclonal antibodies of the present invention to form an exosome complex, and measuring signal intensities ascribed to the complexes; and step (B): judging that it is highly possible to show the drug efficacy of the anticancer agent or the anti-immune disease drug in a case where the signal intensity of the complexes in the biological samples derived from the individual to be tested after administration of the anticancer agent or the anti-immune disease drug is recognized to be weaker than the signal intensity ascribed to the biological sample in the individual before administration of the anticancer agent or the anti-immune disease drug.

For the measurement of the signal intensity ascribed to the complexes in the step (A) of the above-mentioned method for evaluating drug efficacy, a method well known to one skilled in the art can be used so long as the method is a method using a set of monoclonal antibodies of the present invention, and a sandwich ELISA method is preferred.

In the step (B), regarding the signal intensity obtained the above, a comparison is made by carrying out a statistical analysis on the basis of the signal in a biological sample before administration of the anticancer agent or the anti-immune disease drug. The analysis method is not particularly limited, and a known method can be used. In addition, in the subsequent judgment, for example, it is judged that it is highly possible that the anticancer agent or the anti-immune disease drug has an effect of inhibiting cancer or an immune disease in a case where the amount of signal of the biological sample after administration of the anticancer agent or the anti-immune disease drug is less than the signal in the biological sample before the administration.

(Kit for Evaluating Drug Efficacy of Anticancer Agent or Anti-Immune Disease Drug)

In another embodiment of the present invention, a kit for evaluating drug efficacy of an anticancer agent or an anti-immune disease drug is provided.

The kit of the present invention includes a kit containing a set of monoclonal antibodies of the present invention, and the above-mentioned kit can be used for a detection method using a set of monoclonal antibodies of the present invention when detecting exosomes in a sample. Since the set of monoclonal antibodies of the present invention can detect exosomes in a living body with excellent sensitivity and specificity, use of the kit can contribute much to the evaluation of drug efficacy of an anticancer agent or an anti-immune disease drug.

EXAMPLES

The present invention will be explained on the basis of Examples hereinbelow, without intending to limit the present invention to these Examples and the like.

Example 1

Preparation of Anti-CD9 and CD63 Monoclonal Antibodies (Preparation of Antigen)

Partial peptides of CD9 and CD63 proteins, in other words, two kinds of peptides having addition of a cysteine residue to each of the amino terminals of Arg36-Asn50 of CD9 polypeptide and Val38-Pro54 of CD63 polypeptide, were synthesized by Sigma-Aldrich Co. LLC. A hapten antigen was prepared via an SH group of the peptides using these peptides-maleimide activated KLHs [Keyhole Limpet Hemocyanin, Imject™ Maleimide Activated mcKLH, manufactured by Thermo Fischer Scientific Inc.]. The structure of tetraspanin family (CD9 and CD63) is schematically shown in FIG. 2A, and the antigen is schematically shown in FIG. 2B. In addition, the sequences of the peptides are shown in FIG. 3A.

In addition, a fusion protein of Fc region of rabbit IgG and each of large loop portions of CD9 and CD63 was also prepared as an antigen (Fc fusion protein). The information of the antigen is shown in FIG. 2C and FIG. 3B. Concretely, the Fc fusion protein was prepared by introducing a plasmid vector having an insertion of a polynucleotide sequence of Fc added to a carboxyl terminal of the large loop of each of the CD antigens into Freestyle 293-F Cells (manufactured by Invitrogen Corporation) to transiently express a polypeptide, and thereafter purifying the polypeptide using a protein A column (MAPS II Kit, Bio-Rad Laboratories, Inc.).

(Preparation of Monoclonal Antibody)

The hapten antigens of CD9 and CD63 and the Fc fusion protein were mixed with a complete adjuvant for a first immunization, and with an incomplete adjuvant for second or later immunizations in an equal volume, whereby an emulsifying agent as an immunogen was prepared.

The monoclonal antibody was prepared by a method described in K. Watanabe et al., Vasohibin as an endothelium-derived negative feedback regulator of angiogenesis, *J. Clin. Invest.* 114 (2004), 898-907. More particularly, a 5 week-old female A/J type mouse was subcutaneously and intraperitoneally administered with 50 µg of a hapten antigen or 10 µg of Fc fusion protein per mouse per one administration in separated doses of equal volumes. Thereafter, after a fourth or fifth immunization, the spleen was excised from the mouse given with a final booster (4 days before cell fusion), to prepare a spleen cell. The cell fusion of the spleen cell and a myeloma cell (P3U1) was carried out by the method described in K. Watanabe et al., Vasohibin as an endothelium-derived negative feedback regulator of angiogenesis, *J. Clin. Invest.* 114 (2004), 898-907.

(Evaluation of Monoclonal Antibody)

The evaluation of an antibody titer of antisera and hybridoma supernatant (primary evaluation) was carried out in accordance with ELISA method described hereinbelow. Concretely, a 96-well microplate immobilized with a goat anti-mouse IgG antibody was added with antiserum or hybridoma supernatant, and further mixed with a biotinylated CD9 or CD63 protein and HRP-labeled streptavidin. After stirring, the reaction was carried out at room temperature for 2 hours or at 4° C. overnight. After the reaction, the mixture was washed three times with a washing solution (a saline containing 0.01% Tween 20 and 0.1% ProClin 150), and 100 µL of TMB reagent was added thereto. After stirring, the plate was allowed to stand for 15 to 20 minutes, and 50 µL of a 1 N sulfuric acid solution was added thereto, to stop the reaction. The absorbance at 450 nm was measured with ARVO MX (manufactured by PerkinElmer Inc.). When a signal intensity exceeding three times the signal obtained in a case without addition of antisera or hybridoma was observed, it was judged as being positive.

Each of the obtained monoclonal antibodies was purified from a serum-free medium of an antibody-producing hybridoma, or the ascites obtained by administering a hybridoma to a mouse, using a protein A column (MAPS II kit, Bio-Rad Laboratories Inc.). As described above, all of the monoclonal antibodies described were prepared.

Example 2

Confirmation of Reactivity of Monoclonal Antibody Obtained by Immunization with Hapten Antigen or Fc Fusion Protein to Membrane Surface Protein: Secondary Evaluation (Exosome ELISA)

Using MembranePro functional protein expression kit of Invitrogen Corporation, VLPs (virus-like particles) coexpressing CD9 or CD63 and type I membrane protein TEM7 were prepared. Concretely, a 293FT cell (manufactured by Invitrogen Corporation) was transfected with a plasmid vector having insertion of CD9 or CD63 and TEM7 genes into pEF V5-His TA Vector Kit by Lipofectamine 2000. Precipitation Mix reagent was added to the transfected culture supernatant, to precipitate the VLPs. Expression of TEM7 and each of the CD antigens in the VLPs was confirmed by Western blotting (WB) (the results not being shown).

Figures 3, 4:
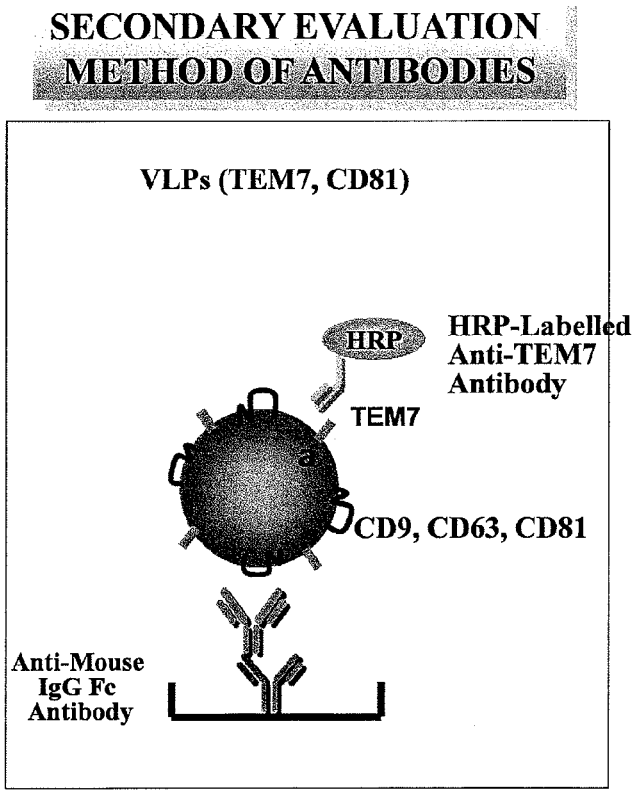
FIG. 3 is the sequence information of CD9 and CD63 used as an antigen.
FIG. 4 shows a method for evaluation using VLPs (Virus-Like-Particles) of a monoclonal antibody (VLP ELISA).
Figure 5:
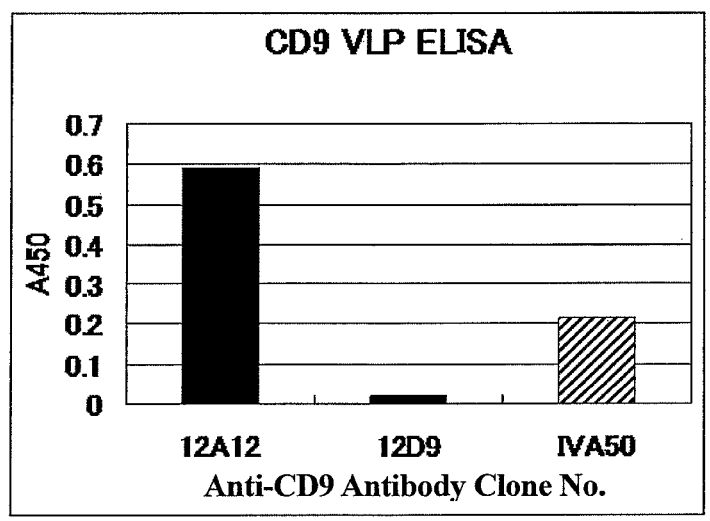
FIG. 5 is a graph for a secondary evaluation of an anti-CD9 monoclonal antibody.
Figure 6:
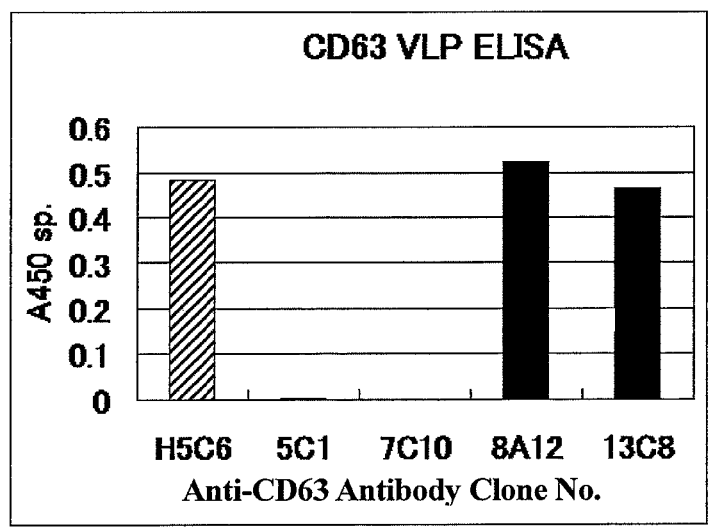
FIG. 6 is a graph for a secondary evaluation of an anti-CD63 monoclonal antibody.

Next, sandwich ELISA was carried out as shown in FIG. 4 using VLPs prepared as described above. Concretely, a plate immobilized with anti-mouse IgG antibody was added with the above-mentioned VLPs, and further added with each of the anti-CD antibodies and HRP-labeled TEM7 antibody Fab', and a reaction was carried out at 4° C. overnight. As a comparative control, a well added with a commercially available anti-CD antibody was also prepared. After the overnight reaction, the mixture was washed with a washing solution, and thereafter 100 µL of a TMB solution was added thereto. After stirring, the mixture was allowed to stand for 15 to 20 minutes, and 50 µL of a 1 N sulfuric acid solution was added thereto, to stop the reaction. The absorbance at 450 nm was measured with ARVO MX (manufactured by PerkinElmer Inc.). Here, as the commercially available antibody, an antibody which recognizes the steric structure was respectively selected according to VLP ELISA. As an anti-CD9 antibody, an antibody manufactured by Abnova Corporation (clone IVA50) was used, and as anti-CD63 antibody, an antibody manufactured by Becton, Dickinson and Company (clone H5C6) was used. The results of the absorbance are shown in FIGS. 5 and 6, respectively.

As a result, it was found that a CD9-12A12 antibody, a CD63-8A12 antibody and a CD63-13C8 antibody could sterically capture exosomes with a reactivity of the same degree as or more than that of a commercially available antibody, in other words, a commercially available antibody which recognizes the steric structure usable for FACS.

Example 3

Combination of Anti-CD9 and Anti-CD63 Monoclonal Antibodies

In order to search for a combination of antibodies in a sandwich ELISA method which allows measurement of exosomes in blood, an immobilized antibody and a labeled antibody were prepared regarding all of the monoclonal antibodies obtained in Example 1 mentioned above, and a sandwich ELISA for measuring exosomes in blood was carried out.

First, a 96-well microplate on which all of the above-mentioned monoclonal antibodies were immobilized was furnished. Concretely, the 96-well microplate was added with 100 µL/well of each of the antibody solutions prepared to have a concentration of 10 µg/mL with a phosphate buffered saline (PBS), to carry out the reaction overnight. Thereafter, the liquid reaction mixture was removed, and the microplate was washed three times with a washing solution (a saline containing 0.01% Tween 20 and 0.1% ProClin 150). After the washing, 2% Block Ace (manufactured by Dainippon Sumitomo Pharma Co., Ltd.) was added thereto in an amount of 200 µL/well, and the mixture was allowed to stand at 4° C. overnight, thereby carrying out blocking. On the other hand, the labeled antibody was prepared by reacting all of the antibodies shown in Tables 3 to 4 with Sulfo-NHS-LC-Biotin (manufactured by Thermo Fischer Scientific Inc.) in an amount 20 times the molar amount of the antibodies and subjecting the mixture to gel filtration with a PD-10 column (manufacture by GE Healthcare).

Next, the plate on which each antibody was immobilized was added with 25 µL of an exosomal solution (0 to 25 µg/mL), and thereafter added with 50 µL of a solution containing a 1 µg/mL labeled antibody prepared as described above and a 0.4 µg/mL HRP (Horseradish Peroxidase)-labeled streptavidin while stirring, and thereafter a reaction was carried out at 4° C. overnight. Thereafter, the liquid reaction mixture was removed, and the microplate was washed three times with the above-mentioned washing solution. Thereafter, 100 μL of TMB solution (Colorburst Blue, manufactured by ALerCHEK, Inc.) was added thereto, a reaction was carried out at room temperature for 15 minutes. Fifty microliters of 1 N sulfuric acid was added thereto to stop the reaction, and the absorbance at 450 nm of each well was measured. Based on the numerical values of the absorbance, the evaluation was carried out as follows: the best combination (a combination of which sensitivity was 100 ng/mL or more and having the best sensitivity in each group) was ranked as "◎,"
a combination with which an assay can be carried out (of which sensitivity was 100 ng/mL or more) was ranked as "○,"
a combination with which weak reactivity was observed (of which sensitivity was less than 100 ng/mL) was ranked as "Δ,"
a combination with which reactivity was not observed was ranked as "x," and
a combination which was not examined was ranked as "–."
The results are shown in Tables 3 and 4. Here, as a commercially available antibody, the same antibody as in Example 2 was used.

TABLE 3

[Anti-CD9 Antibody]

| | | Immobilized Antibody | | |
|---|---|---|---|---|
| | | IVA50 (Commercially Available) | 12A12 | 12D9 |
| Labeled Antibody | IVA50 (Commercially Available) | Δ | ○ | X |
| | 12A12 | Δ | ◎ | X |
| | 12D9 | X | X | X |

TABLE 4

[Anti-CD63 Antibody]

| | | Immobilized Antibody | | | | |
|---|---|---|---|---|---|---|
| | | H5C6 (Commercially Available) | 5C1 | 7C10 | 8A12 | 13C8 |
| Labeled Antibody | H5C6 (Commercially Available) | Δ | X | X | ○ | ○ |
| | 5C1 | X | X | X | X | X |
| | 7C10 | X | X | X | X | X |
| | 8A12 | ○ | X | X | ○ | ○ |
| | 13C8 | ○ | X | X | ◎ | ○ |

As a result, the following combination of the antibodies prepared in the invention of the present application was found out to be the best combination in any of the exosome ELISAs using the anti-CD9 and anti-CD63 monoclonal antibodies.
immobilized antibody: CD9-12A12 antibody, labeled antibody: CD9-12A12 antibody
immobilized antibody: CD63-8A12 antibody, labeled antibody: CD63-13C8 antibody
In addition, it is known that an antibody appropriate to be used as an immobilized antibody in a combination with a particular labeled antibody is generally also appropriate to be used as an immobilized antibody in a combination with other labeled antibodies. Similarly, it is known that an antibody appropriate to be used as a labeled antibody in a combination with a particular immobilized antibody is generally also appropriate to be used as a labeled antibody in a combination with other immobilized antibodies.

Therefore, based on the above-mentioned experimental results, it can be sufficiently predicted that the following combinations are similarly good combinations.
immobilized antibody: CD9-12A12 antibody, labeled antibody: CD63-13C8 antibody,
immobilized antibody: CD63-8A12 antibody, labeled antibody: CD9-12A12 antibody As described above, the commercially available antibody and the antibody of the present invention are summarized in Tables 5 and 6. Here, from the above-mentioned results, antibody appropriateness was evaluated as follows:
an extremely strong antibody (optimal antibody) was ranked as "◎,"
an antibody which is usable was ranked as "○,"
an antibody having weak reactivity was ranked as "Δ," and
an antibody which is not usable was ranked as "x."

TABLE 5

[Anti-CD9 Antibody]

| Clone No. | Immunogen | Subclass | Appropriateness as Labeled Antibody | Appropriateness as Immobilized Antibody |
|---|---|---|---|---|
| IVA50 (Commercially Available) | Bovine Blood Platelet | IgG2a | ○ | ○ |
| 12A12 | Large Loop | IgG2b | ◎ | ◎ |
| 12D9 | CD9 | IgG2b | X | X |

TABLE 6

[Anti-CD63 Antibody]

| Clone No. | Immunogen | Subclass | Appropriateness as Labeled Antibody | Appropriateness as Immobilized Antibody |
|---|---|---|---|---|
| H5C6 (Commercially Available) | CD63 | IgG1 | ○ | Δ |
| 5C1 | Large | IgG1 | X | X |
| 7C10 | Loop | IgG2a | X | X |
| 8A12 | CD63 | IgG2a | ◎ | ○ |
| 13C8 | | IgG1 | ○ | ◎ |

Example 4

Construction of ELISA Method of Exosome Using Anti-CD9 and Anti-CD63

In order to further improve the sensitivity of the best combination of antibodies selected in Example 3, an ELISA method was constructed using a labeled antibody prepared by carrying out direct labelling on the antibody.

First, an antibody appropriate for detection was subjected to alkaline phosphatase (ALP) labeling. Regarding CD9-12A12 antibody of subclass IgG2b, which cannot be cleaved into Fab' by pepsin digestion, ALP labeling was carried out via an SH group generated by reducing IgG using Alkaline Phosphatase Labeling Kit-SH (ALP labeling reagent, manufactured by DOJINDO LABORATORIES).

In addition, regarding CD63-13C8 antibody, which is a subclass IgG2a, after preparation of Fab', enzyme labeling was carried out using a hinge method. In other words, digestion was carried out by reacting 50 μg of pepsin with 1 mg of the antibody to prepare F(ab')2, and thereafter purification by gel filtration using a TSKgel G2000SWXL column of HPLC (manufactured by TOSOH CORPORATION) was carried out. Next, Fab' was prepared by reduction by 10 mM 2-mercaptoethylamine and the above-mentioned column. On the other hand, ALP was maleimidated by Sulfo-HMCS, and purified with a PD-10 column (manufactured by GE Healthcare). The Fab' and the maleimidated ALP were mixed in equal molar amounts, and reaction was carried out at 4° C. overnight. Thereafter, purification was carried out with the above-mentioned TSKgel G2000SWXL column of HPLC, to prepare a labeled antibody.

Figure 7:
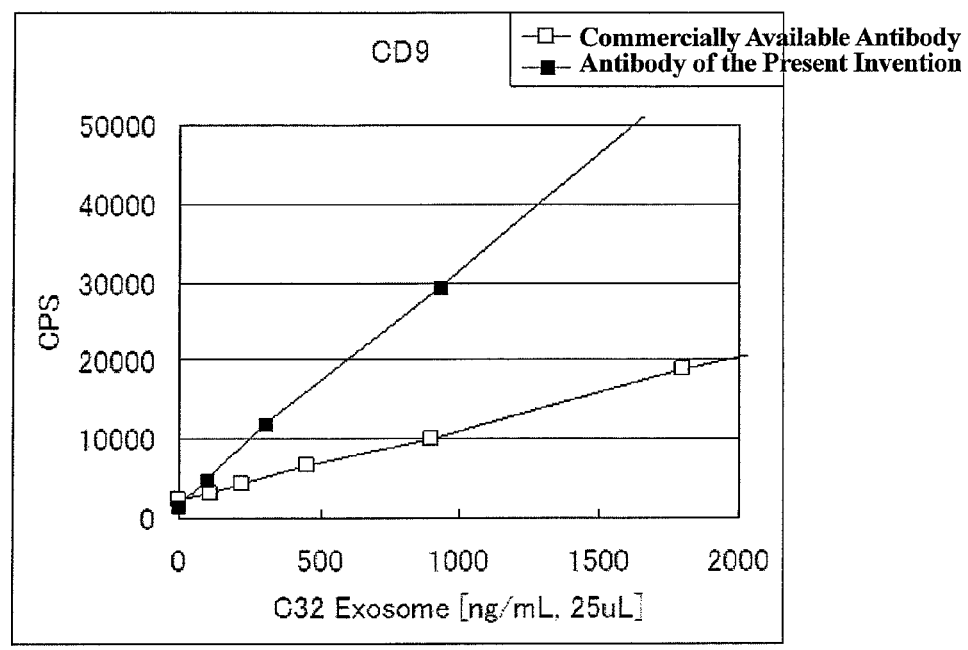
FIG. 7 is a graph showing a standard curve of exosome ELISA of CD9.

Concretely, regarding CD9, a plate on which CD9-12A12 antibody was immobilized was previously added with 75 μL of assay buffer (50 mM Tris-HCl buffered saline containing 1 mM magnesium chloride, 0.1 mM calcium chloride, 0.5% BSA and 1% BSA, pH 7.4), and then added with 25 μL of an exosomal standard solution (0 to 25 μg/mL), and a reaction was carried out at room temperature for 2 hours with shaking the mixture. After the plate was washed three times with a washing solution (a saline (0.9% NaCl) containing 0.01% Tween 20 and 0.05% ProClin 150), and thereafter 100 μL of a 2.5 ng/mL ALP-labeled CD9-12A12 antibody was added thereto. Thereafter, the mixture was stirred, and thereafter allowed to react at room temperature for 3 hours. Thereafter, the liquid reaction mixture was removed, and the plate was washed four times with the above-mentioned washing solution, and thereafter 100 μL of chemiluminescent substrate solution (Lumigen APS-5) was added thereto. After stirring the mixture, the amount of chemiluminescence of each well was measured. The results are shown in FIG. 7.

Figure 8:
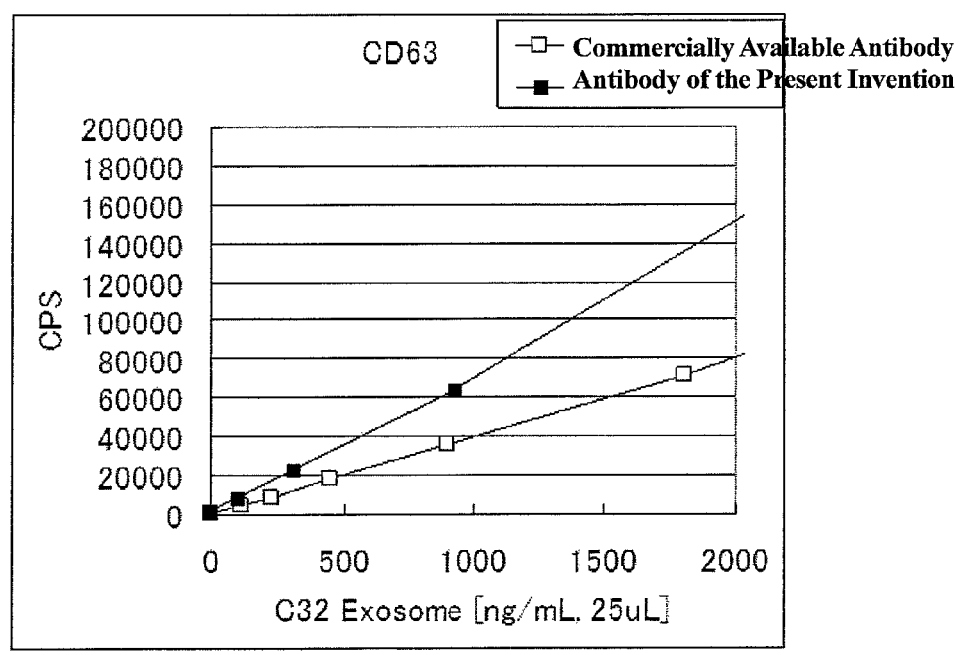
FIG. 8 is a graph showing a standard curve of exosome ELISA of CD63.

Regarding CD63, reaction with a biotinylated CD63-8A12 antibody was previously carried out at a concentration of 1 μg/mL at 4° C. overnight. After three times of washing with the same washing solution as that for CD9, 75 μL of the above-mentioned assay buffer was added thereto. Twenty-five milliliters of exosome standard solution (0 to 25 μg/mL) was added thereto, and reaction was carried out at room temperature for 2 hours with shaking the mixture. After washing with the above-mentioned washing solution for three times, 100 μL of a 12.5 ng/mL ALP-labeled CD63-13C8 antibody was added thereto. Thereafter, the mixture was stirred, and thereafter allowed to react at room temperature for 3 hours. Thereafter, the liquid reaction mixture was removed, and the plate was washed four times with the above-mentioned washing solution, and thereafter 100 μL of the above-mentioned chemiluminescent substrate solution was added thereto. After stirring the solution, the amount of chemiluminescence of each well was measured. The results are shown in FIG. 8.

As a result, in any of exosome ELISAs using the anti-CD9 or anti-CD63 monoclonal antibody, 2.5 ng/assay (100 ng/mL) of exosomes could be detected. Regarding the detection by exosome ELISA method, it has been reported that 3 μg of exosomes could be detected in M. Logozzi et al., High Levels of exosomes Expressing CD63 and Caveolin-1 in Plasma of Melanoma Patients, *PLoS One.* 4 (2009), 1-10. On the other hand, exosome ELISAs of any of the anti-CD9 and anti-CD63 antibodies constructed this time can detect 2.5 ng of exosomes, of which sensitivity is higher than the reported exosome ELISA by a three-order magnitude. In addition, in any of exosome ELISAs, sensitivity was higher as compared with that in exosome ELISA using commercially available antibodies.

Furthermore, a recovery test was carried out regarding the above-mentioned exosome ELISA using the combination of the anti-CD9 antibodies and the combination of the anti-CD63 antibodies of the present invention, to evaluate the specificity of the binding. Concretely, additional recovery of exosomes derived from C32 melanoma cells to a serum specimen was examined. As a result, excellent additional recovery rates were obtained such that 87.9 to 113.4% additional recovery rate was obtained in a case where the anti-CD9 antibody was used and 96.2 to 99.3% additional recovery rate was obtained in a case where the anti-CD63 antibody was used. On the other hand, in exosome ELISA using a commercially available anti-CD9 antibody, the obtained additional recovery rate was 32.1 to 41.8%, which was not sufficient. Here, as a commercially available antibody, the same antibody as in Example 2 was used.

Example 5

Figure 9:
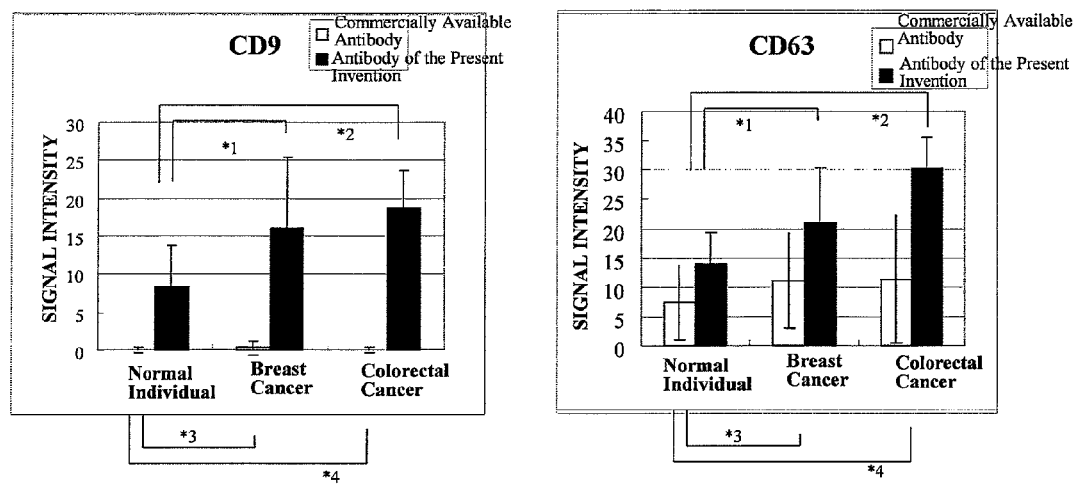
FIG. 9 is a graph of comparing signal intensities ascribed to exosomes in sera of a normal individual, a patient with breast cancer, and a patient with colorectal cancer by exosome ELISA with an anti-CD9 antibody or an anti-CD63 antibody, which is commercially available or that of the present invention (made in house).

Detection of Exosome in Blood Specimen from Cancer Patient by Anti-CD9 and Anti-CD63 Antibodies The amount of exosomes in sera from 10 individuals each of normal individuals, patients with breast cancer, and patients with colorectal cancer was measured using the combination of immobilized antibody: CD9-12A12 antibody, labeled antibody: CD9-12A12 antibody and the combination of immobilized antibody: CD63-8A12 antibody, labeled antibody: CD63-13C8 antibody, according to exosome ELISA in the same manner as in Example 4. The results are shown in FIG. 9. Here, comparison between the groups was carried out by t-test.

As a result, in the exosome ELISA using the anti-CD9 antibody, both of the patients with breast cancer, and the patients with colorectal cancer showed significantly high values as compared with that of the normal individuals. In addition, in the exosome ELISA using the anti-CD63 antibody, similar results were obtained. Accordingly, it is suggested that exosome ELISA using the combination of the anti-CD9 antibodies and the combination of the anti-CD63 antibodies of the present invention can be applied to diagnosis of breast cancer, and colorectal cancer. On the other hand, in the exosome ELISA using a commercially available antibody (anti-CD9 antibody or anti-CD63 antibody), significant difference was not observed. Here, as a commercially available antibody, an antibody manufactured by Abnova Corporation (clone IVA50) was used as an anti-CD9 antibody, and an antibody manufactured by Santa Cruz Biotechnology, Inc. (sc-5275) was used as an anti-CD63 antibody.

Furthermore, an exosome ELISA using a combination of an anti-CD9 antibody and an anti-CD63 antibody was constructed, and exosomes in sera of normal individuals, patients with breast cancer, and patients with colorectal cancer were measured in the same manner. Concretely, the measurement was carried out using a combination of immobilized antibody: CD9-12A12 antibody, labeled antibody: CD63-8A12 antibody and a combination of immobilized antibody: CD63-13C8 antibody, labeled antibody: CD9-

Figure 10:
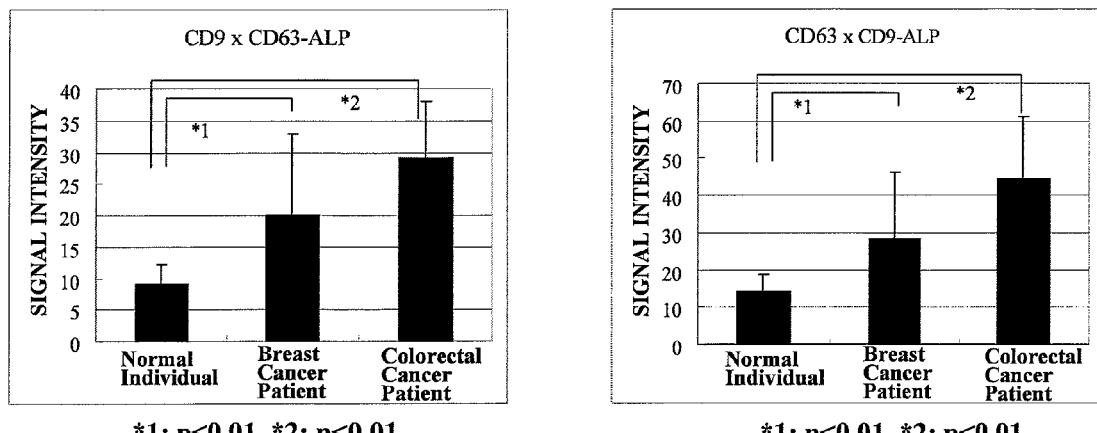
FIG. 10 is a graph of measurement of signal intensities ascribed to exosomes in sera of normal individuals, a patient with breast cancer, and a patient with colorectal cancer by exosome ELISA using an anti-CD9 antibody and an anti-CD63 antibody of the present invention in combination.

12A12 antibody. The results are shown in FIG. 10. Here, as both of the labeled antibodies, an antibody directly labeled with ALP was used.

As shown in the left (immobilized antibody: anti-CD9 antibody, ALP-labeled antibody: anti-CD63 antibody) and right (immobilized antibody: anti-CD63 antibody, ALP-labeled antibody: anti-CD9 antibody) of FIG. 10, differences between the cancer patients and the normal individuals are large in both cases, and significantly high values were shown in both of the patients with breast cancer and the patients with colorectal cancer.

Example 6

Diagnostic Application of Exosome ELISA Using Combination of Antibodies Against Disease-Specific Membrane Protein Possibility of exosomal quantification associated with cancer was evaluated by combining the anti-CD9 or anti-CD63 antibody mentioned above with an antibody against a disease-specific membrane protein. Concretely, EpCAM antibody was selected as an antibody against a membrane protein associated with cancer, and an antibody manufactured by Abcam plc. (clone AUA1) was used.

Here, before carrying out exosome ELISA, it was previously confirmed that EpCAM was strongly expressed in a cell lysate or in exosomes in a culture supernatant in breast cancer cell lines (ZR75-1, T47D, MCF7, BT474 and MDA-MB-468), colorectal cancer cell lines (HT29, SW48, SW480 and HCT116) and the like. On the other hand, it was confirmed that the expression was not observed in a normal mammary cell 184A1 (the results not shown).

Figures 11, 12:
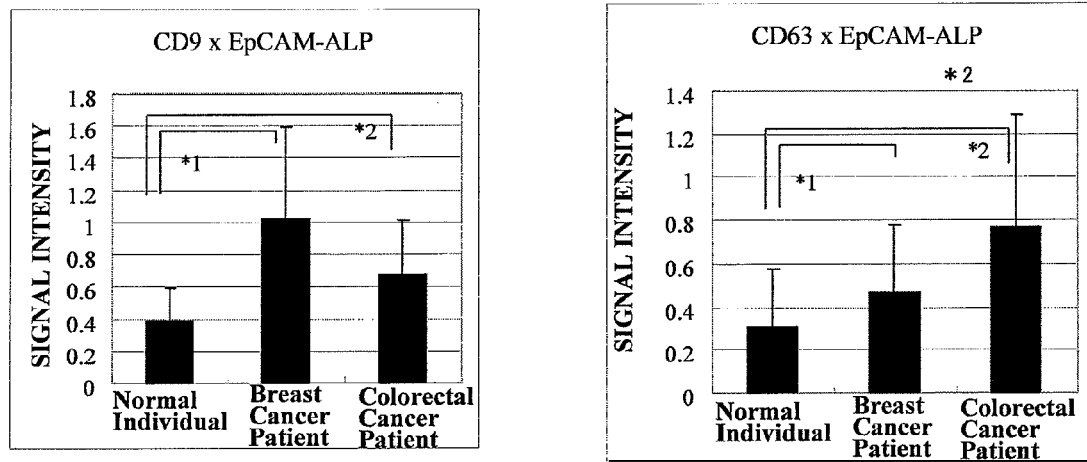
FIG. 11 is a graph of measurement of a signal intensity ascribed to exosomes in sera of normal individuals, a patient with breast cancer, and a patient with colorectal cancer by exosome ELISA using an anti-CD9 antibody or an anti-CD63 antibody of the present invention in combination with an anti-EpCAM antibody.
FIG. 12 is the sequence information of CD81 used as an antigen.

In order to construct exosome ELISA using an anti-EpCAM antibody, an EpCAM antibody was subjected to ALP labelling using Alkaline Phosphatase Labeling Kit-SH (ALP labeling reagent, manufactured by DOJINDO LABORATORIES). A blood specimen directed to exosomes derived from a colorectal cancer cell line HCT116 was quantified by carrying out exosome ELISA using an ALP-labeled EpCAM antibody and an anti-CD9 or anti-CD63 antibody as an immobilized antibody. The results are shown in FIG. 11. Here, comparison between the groups was carried out by t-test.

As a result, it was found that some exosome ELISA showed a significantly higher value in either or both of the patients with breast cancer and patients with colorectal cancer as compared to that of normal individuals. The results are data showing possibility that a membrane protein which has been so far difficult to be applied to diagnosis can be applied as a diagnostic marker by the exosome ELISA using a combination of an antibody against a membrane protein associated with a disease such as cancer with an anti-CD9 or anti-CD63 antibody.

Example 7

Preparation of Anti-CD81 Monoclonal Antibody (Preparation of Antigen)
In order to further produce anti-CD81 antibody, a small loop peptide of CD81, in other words, a peptide having addition of a cysteine residue to the amino terminal of Arg36-Ala54 of CD81 polypeptide was synthesized by Sigma-Aldrich Co. LLC. A hapten antigen was prepared via an SH group in the peptide using these peptides and maleimide activated KLHs [Keyhole Limpet Hemocyanin, Imject™ Maleimide Activated mcKLH, manufactured by Thermo Fischer Scientific Inc.]. The structure of tetraspanin family (CD9, CD63 and CD81) is schematically shown in FIG. 2A, and the antigen is schematically shown in FIG. 2B. In addition, the sequence of the peptide is shown in FIG. 12A.

In addition, a fusion protein of Fc region of rabbit IgG and a large loop portion of CD81 (Fc fusion protein) was also prepared as an antigen. The information of the antigen is shown in FIG. 2C and FIG. 12B. In other words, the Fc fusion protein was prepared by introducing a plasmid vector having an insertion of a polynucleotide sequence of Fc added to a carboxyl terminal of the large loop of the CD antigen into Freestyle 293-F Cells (manufactured by Invitrogen Corporation) to transiently express the polypeptide, and thereafter purifying the polypeptide using a protein A column (MAPS II Kit, Bio-Rad Laboratories, Inc.).

(Preparation of Monoclonal Antibody)
The hapten antigens and Fc fusion protein of CD81 were mixed with a complete adjuvant for a first immunization, and with an incomplete adjuvant for second or later immunizations in an equal volume, whereby an emulsifying agent as an immunogen was prepared.

The monoclonal antibody was produced by the method described in K. Watanabe et al., Vasohibin as an endothelium-derived negative feedback regulator of angiogenesis, *J. Clin. Invest.* 114 (2004), 898-907. In other words, a 5 week-old female A/J type mouse was subcutaneously or intraperitoneally administered with 50 µg of a hapten antigen or 10 µg of Fc fusion protein per mouse per one administration in separated doses of equal volumes. Thereafter, after a fourth or fifth immunization, the spleen was excised from the mouse given with a final booster (4 days before cell fusion), to prepare spleen cells. The cell fusion of the spleen cells and myeloma cells (P3U1) was carried out by the method described in K. Watanabe et al., Vasohibin as an endothelium-derived negative feedback regulator of angiogenesis, *J. Clin. Invest.* 114 (2004), 898-907.

(Evaluation of Monoclonal Antibody)
The evaluation of an antibody titer of antisera and hybridoma supernatant (primary evaluation) was carried out in accordance with ELISA method described hereinbelow. Concretely, a 96-well microplate immobilized with a goat anti-mouse IgG antibody was added with antiserum or hybridoma supernatant, and further mixed with a biotinylated CD81 protein and HRP-labeled streptavidin while stirring. Thereafter, the reaction was carried out at room temperature for 2 hours or at 4° C. overnight. After the reaction, the microplate was washed three times with a washing solution (a saline containing 0.01% Tween 20 and 0.1% ProClin 150), and 100 µL of TMB reagent was added thereto. After stirring, the reagent was allowed to stand for 15 to 20 minutes, and 50µL of 1 N sulfuric acid solution was added thereto, to stop the reaction. The absorbance at 450 nm was measured with ARVO MX (manufactured by PerkinElmer Inc.). When a signal intensity exceeding three times the signal obtained in a case where antisera or hybridoma was not added was observed, the sample was judged as being positive.

Each of the obtained monoclonal antibodies was purified from a serum-free medium of an antibody-producing hybridoma, or the ascites obtained by administering a hybridoma to a mouse, using a protein A column (MAPS II kit, Bio-Rad Laboratories Inc.). As described above, all of the anti-CD81 monoclonal antibodies described later were prepared.

Example 8

Capture of Exosomes by Immunoprecipitation with Anti-CD9, Anti-CD63 and Anti-CD81 Antibodies Possibility of purification of exosomes by immunoprecipitation using the anti-CD9, anti-CD63 and anti-CD81 monoclonal antibodies obtained in Examples 1 and 7 was evaluated. Here, as a commercially available antibody used for comparison, an antibody of which immunoprecipitation ability is more excellent among any of the given three commercially available antibodies was selected and used. Concretely, as anti-CD9 antibody, an antibody of Abnova Corporation (IVA50) was used, and as anti-CD63 antibody, an antibody of EXBIO (MEM-259) and an antibody of Becton, Dickinson and Company (H5C6) were used. As anti-CD81 antibody, an antibody of GeneTex Inc. (1D6) was used.

As samples used for immunoprecipitation, the following samples were used. Regarding the anti-CD63 antibody and anti-CD81 antibody, exosomes prepared from a culture supernatant of COS7 cells into which plasmids having addition of a FLAG tag to the C-terminals of a polynucleotide encoding a CD63 or CD81 polypeptides were introduced were used. Regarding the CD9 antibody, sera of normal individuals were used.

Immunoprecipitation was carried out as follows.

Figure 13:
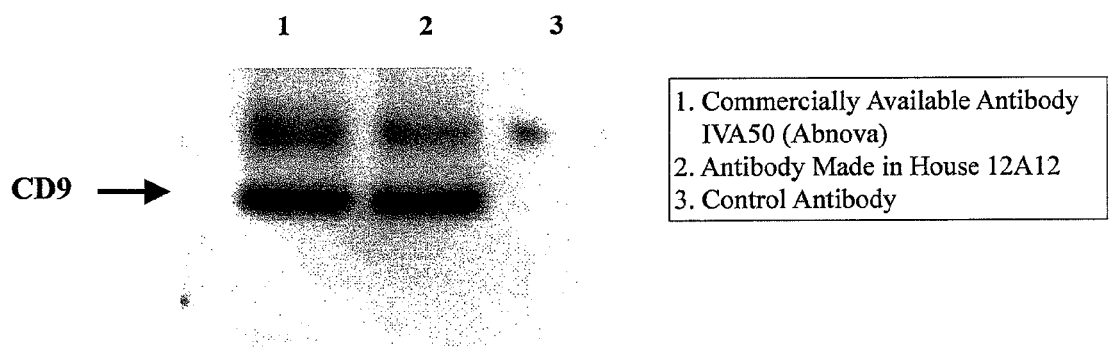
FIG. 13 is a figure of comparison in the properties of immunoprecipitation of an anti-CD9 antibody of the present invention to that of a commercially available anti-CD9 antibody.
Figure 14:
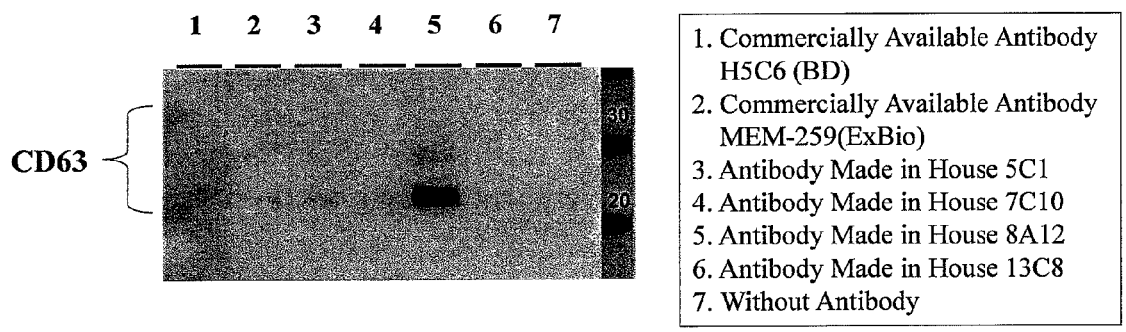
FIG. 14 is a figure of comparison in the properties of immunoprecipitation of anti-CD63 antibodies of the present invention to that of commercially available anti-CD63 antibodies.
Figure 15:
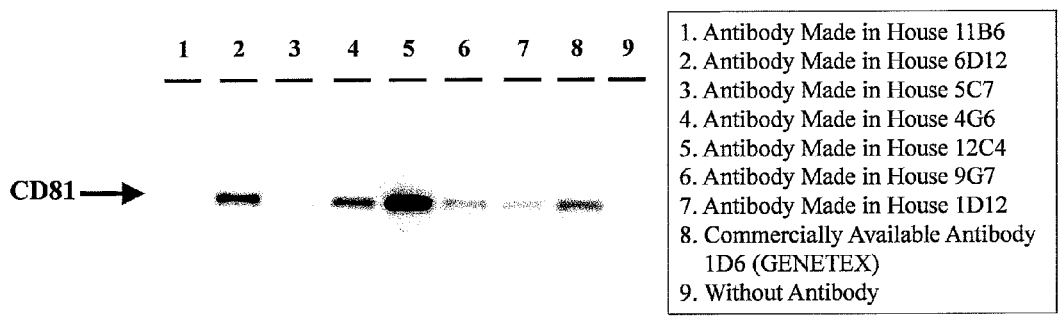
FIG. 15 is a figure of comparison in the properties of immunoprecipitation of the anti-CD81 antibody of the present invention to that of a commercially available anti-CD81 antibody.

In a case of the anti-CD63 or anti-CD81 antibody, 1 µg of the antibody was added to 1 µg of an exosomal solution dissolved in PBS solution containing 1 % BSA, and a reaction was carried out at 4° C. overnight. After adding 20 µL of Protein G agarose (50% slurry) thereto, reaction was carried out at 4° C. for 2 hours while stirring the mixture. After the reaction, the beads were subjected twice to centrifugal washing with PBS containing 1% BSA, and thereafter evaluation of the amount of CD63 or CD81 on the exosomes captured by beads was carried out by Western blotting (WB) using HRP-labeled anti-FLAG antibody. Regarding the anti-CD9 antibody, 100 µL of PBS containing 1% BSA was added to 100 µL of sera, and M280 magnetic beads immobilized with the anti-CD9 antibody were added thereto in an amount equivalent to 1 µg of the antibody, and a reaction was carried out at 4° C. overnight. After the reaction, the beads were washed with PBS containing 1% BSA using a magnet, and the evaluation of the amount of CD9 on the exosomes captured by the beads was carried out by WB using the anti-CD9 antibody and the HRP-labeled anti-mouse IgG antibody. The figures of comparison of the properties of immunoprecipitation of exosomes by each of the anti-CD antibodies are shown in FIGS. 13, 14 and 15.

As a result, the CD9-12A12 antibody, CD63-8A12 antibody, CD81-6D12 antibody, CD81-4G6 antibody and CD81-12C4 antibody showed immunoprecipitation ability of exosomes higher than that of commercially available antibodies.

Example 9

Diagnosis of a Disease According to Detection of miRNA Derived from Captured Exosomes From the exosomes captured by referring to the method of Example 8, miRNA or a protein is detected in accordance with a known method. The detected miRNA or protein can be analyzed in accordance with a known method, thereby making it possible to analyze physiological phenomena and to judge that it is suffering from a particular disease.

The miRNA in exosomes can be analyzed by microarray analysis or quantitative PCR, referring to, for example, K. Ohshima, et al, PLoS One, 2010, 5, 1-10.

INDUSTRIAL APPLICABILITY

The monoclonal antibody for detecting exosomes of the present invention is capable of detecting CD9, CD63 or CD81 on exosomes in a living body with excellent sensitivity and specificity. Accordingly, for example, by carrying out quantification of exosomes in combination with an antibody against a disease-specific membrane protein, diagnosis of a specific disease can be made, so that applications to a diagnostic drug is expected. Furthermore, it is shown that the monoclonal antibody of the present invention can purify exosomes by immunoprecipitation, and development of a diagnostic drug to which a fluctuation in miRNA or a protein in exosomes is applied is also expected.

SEQUENCE FREE TEXT

SEQ ID NO: 1 of the Sequence Listing is an exosome membrane protein, CD9 polypeptide.

SEQ ID NO: 2 of the Sequence Listing is an exosome membrane protein, CD63 polypeptide.

SEQ ID NO: 3 of the Sequence Listing is an exosome membrane protein, CD81 polypeptide.

---

The invention claimed is:

1. A monoclonal antibody for detecting or capturing an exosome selected from the group consisting of:

a monoclonal antibody (CD9-12A12 antibody) produced by a hybridoma deposited under Accession Number FERM BP-11519 or fragments thereof which are monoclonal antibody fragments that recognize amino acid numbers 113 to 195 of the amino acid sequence as shown in SEQ ID NO: 1;

a monoclonal antibody (CD63-8A12 antibody) produced by a hybridoma deposited under Accession Number FERM BP-11520 or fragments thereof which are monoclonal antibody fragments that recognize amino acid numbers 104 to 202 of the amino acid sequence as shown in SEQ ID NO: 2;

a monoclonal antibody (CD63-13C8 antibody) produced by a hybridoma deposited under Accession Number FERM BP-11521 or fragments thereof which are monoclonal antibody fragments that recognize amino acid numbers 104 to 202 of the amino acid sequence as shown in SEQ ID NO: 2;

a monoclonal antibody (CD81-4G6 antibody) produced by a hybridoma deposited under Accession Number NITE BP-1480 or fragments thereof which are monoclonal antibody fragments that recognize amino acid numbers 113 to 201 of the amino acid sequence as shown in SEQ ID NO: 3;

a monoclonal antibody (CD81-6D12 antibody) produced by a hybridoma deposited under Accession Number NITE BP-1481 or fragments thereof which are monoclonal antibody fragments that recognize amino acid numbers 113 to 201 of the amino acid sequence as shown in SEQ ID NO: 3; and a monoclonal antibody (CD81-12C4 antibody) produced by a hybridoma deposited under Accession Number NITE BP-1482 or fragments thereof which are monoclonal antibody fragments that recognize amino acid numbers 36 to 54 of the amino acid sequence as shown in SEQ ID NO: 3.

2. A set of monoclonal antibodies or antibody fragments thereof, comprising a combination of the same or two antibodies or antibody fragments selected from the group consisting of a CD9-12A12 antibody produced by a hybridoma deposited under Accession Number FERM BP-11519 or antibody fragments thereof, a CD63-8A12 antibody produced by a hybridoma deposited under Accession Number FERM BP-11520 or antibody fragments thereof, and a CD63-13C8 antibody produced by a hybridoma deposited under Accession Number FERM BP 11521 or antibody fragments thereof, wherein said antibody fragment of the CD9-12A12 antibody binds to CD9 and recognizes amino acid numbers 113 to 195 of SEQ ID NO: 1, and said antibody fragment of the CD63-8A12 antibody or said antibody fragment of the CD63-13C8 antibody binds to CD63 and recognizes amino acid numbers 104 to 202 of SEQ ID NO: 2.

3. The set according to claim 2, which is selected from the group consisting of:

a set wherein an immobilized antibody is the CD9-12A12 antibody produced by the hybridoma deposited under Accession Number FERM BP-11519 or the antibody fragment thereof, and a labeled antibody is the CD9-12A12 antibody produced by the hybridoma deposited under Accession Number FERM BP-11519 or the antibody fragment thereof;

a set wherein an immobilized antibody is the CD9-12A12 antibody produced by the hybridoma deposited under Accession Number FERM BP-11519 or the antibody fragment thereof, and a labeled antibody is the CD63-13C8 antibody produced by the hybridoma deposited under Accession Number FERM BP-11521 or the antibody fragment thereof;

a set wherein an immobilized antibody is the CD63-8A12 antibody produced by the hybridoma deposited under Accession Number FERM BP-11520 or the antibody fragment thereof, and a labeled antibody is the CD9-12A12 antibody produced by the hybridoma deposited under Accession Number FERM BP-11519 or the antibody fragment thereof; and a set wherein an immobilized antibody is the CD63-8A12 antibody produced by the hybridoma deposited under Accession Number FERM BP-11520 or the antibody fragment thereof, and a labeled antibody is the CD63-13C8 antibody produced by the hybridoma deposited under Accession Number FERM BP11521 or the antibody fragment thereof, wherein said antibody fragment of the CD9-12A12 antibody binds to CD9 and recognizes amino acid numbers 113 to 195 of SEQ ID NO: 1, and said antibody fragment of the CD63-8A12 antibody or said antibody fragment of the CD63-13C8 antibody binds to CD63 and recognizes amino acid numbers 104 to 202 of SEQ ID NO: 2.

4. A set of a monoclonal antibody for detecting a disease-specific exosome, comprising a combination of an antibody or antibody fragments thereof, selected from the group consisting of a CD9-12A12 antibody produced by a hybridoma deposited under Accession Number FERM BP-11519 or antibody fragments thereof, a CD63-8A12 antibody produced by a hybridoma deposited under Accession Number FERM BP-11520 or antibody fragments thereof, and a CD63-13C8 antibody produced by a hybridoma deposited under Accession Number FERM BP-11521 or antibody fragments thereof, and an antibody or antibody fragments thereof against a disease-specific membrane protein, wherein said antibody fragment of the CD9-12A12 antibody binds to CD9 and recognizes amino acid numbers 113 to 195 of SEQ ID NO: 1, and said antibody fragment of the CD63-8A12 antibody or said antibody fragment of the CD63-13C8 antibody binds to CD63 and recognizes amino acid numbers 104 to 202 of SEQ ID NO: 2.

* * * * *

SEQUENCE LISTING

```
<160> NUMBER OF SEQ ID NOS: 3

<210> SEQ ID NO 1
<211> LENGTH: 228
<212> TYPE: PRT
<213> ORGANISM: Homo sapiens

<400> SEQUENCE: 1

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45
```

```
Thr Asn Asn Asn Ser Ser Phe Tyr Thr Gly Val Tyr Ile Leu Ile
    50              55                  60

Gly Ala Gly Ala Leu Met Met Leu Val Gly Phe Leu Gly Cys Cys Gly
65              70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ile Trp Gly Tyr Ser
            100             105             110

His Lys Asp Glu Val Ile Lys Glu Val Gln Phe Tyr Lys Asp Thr
            115             120             125

Tyr Asn Lys Leu Lys Thr Lys Asp Glu Pro Gln Arg Glu Thr Leu Lys
    130             135             140

Ala Ile His Tyr Ala Leu Asn Cys Cys Gly Leu Ala Gly Gly Val Glu
145             150             155                 160

Gln Phe Ile Ser Asp Ile Cys Pro Lys Lys Asp Val Leu Glu Thr Phe
                165             170             175

Thr Val Lys Ser Cys Pro Asp Ala Ile Lys Glu Val Phe Asp Asn Lys
            180             185             190

Phe His Ile Ile Gly Ala Val Gly Ile Gly Ile Ala Val Val Met Ile
            195             200             205

Phe Gly Met Ile Phe Ser Met Ile Leu Cys Cys Ala Ile Arg Arg Asn
    210             215             220

Arg Glu Met Val
225

<210> SEQ ID NO 2
<211> LENGTH: 238
<212> TYPE: PRT
<213> ORGANISM: Homo sapiens

<400> SEQUENCE: 2

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65              70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190
```

```
Glu Lys Ile Gly Gly Trp Leu Arg Lys Asn Val Leu Val Ala Ala
        195             200             205

Ala Ala Leu Gly Ile Ala Phe Val Glu Val Leu Gly Ile Val Phe Ala
    210             215             220

Cys Cys Leu Val Lys Ser Ile Arg Ser Gly Tyr Glu Val Met
225             230             235

<210> SEQ ID NO 3
<211> LENGTH: 236
<212> TYPE: PRT
<213> ORGANISM: Homo sapiens

<400> SEQUENCE: 3

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Ile
50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
                115                 120                 125

Gln Ala Leu Gln Gln Ala Val Val Asp Asp Asp Ala Asn Asn Ala Lys
            130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
                180                 185                 190

Lys Ile Asp Asp Leu Phe Ser Gly Lys Leu Tyr Leu Ile Gly Ile Ala
            195                 200                 205

Ala Ile Val Val Ala Val Ile Met Ile Phe Glu Met Ile Leu Ser Met
            210                 215                 220

Val Leu Cys Cys Gly Ile Arg Asn Ser Ser Val Tyr
225                 230                 235
```